(12) United States Patent
Ishikawa (10) Patent No.: US 7,967,804 B2
(45) Date of Patent: Jun. 28, 2011

(54) DISPOSABLE DIAPER AND PROCESS FOR MAKING THE SAME

(75) Inventor: Hideyuki Ishikawa, Kagawa-ken (JP)

(73) Assignee: Uni-Charm Corporation, Ehime (JP)

( * ) Notice: Subject to any disclaimer, the term of this patent is extended or adjusted under 35 U.S.C. 154(b) by 206 days.

(21) Appl. No.: 12/217,271

(22) Filed: Jul. 2, 2008

(65) Prior Publication Data

US 2008/0275420 A1   Nov. 6, 2008

Related U.S. Application Data

(63) Continuation of application No. 09/864,836, filed on May 24, 2001, now abandoned.

(30) Foreign Application Priority Data

May 30, 2000   (JP) .................................. 2000-160909

(51) Int. Cl.
    *A61F 13/15*   (2006.01)
(52) U.S. Cl. ......... 604/385.22; 604/385.25; 604/385.27; 604/385.26; 604/385.31
(58) Field of Classification Search ............. 604/385.22, 604/385.25, 385.27, 385.26, 385.31
    See application file for complete search history.

(56) References Cited

U.S. PATENT DOCUMENTS

| | | |
|---|---|---|
| 4,655,760 A | 4/1987 | Morman et al. |
| 4,756,709 A | 7/1988 | Stevens |
| 4,834,741 A | 5/1989 | Sabee |
| 4,847,134 A | 7/1989 | Fahrenkrug et al. |
| 5,196,000 A | 3/1993 | Clear et al. |
| 5,226,992 A | 7/1993 | Morman |
| 5,246,433 A | 9/1993 | Hasse et al. |
| 5,575,783 A | 11/1996 | Clear et al. |
| 5,576,090 A | 11/1996 | Suzuki |
| 5,683,787 A | 11/1997 | Boich et al. |
| 5,797,895 A | 8/1998 | Widlund et al. |
| 5,814,569 A | 9/1998 | Suzuki et al. |
| 5,846,232 A | 12/1998 | Serbiak et al. |
| 5,853,881 A | 12/1998 | Estey et al. |
| 5,885,908 A | 3/1999 | Jaeger et al. |
| 5,997,989 A | 12/1999 | Gessner et al. |
| 6,340,782 B1 | 1/2002 | Kling et al. |

FOREIGN PATENT DOCUMENTS

| | | |
|---|---|---|
| EP | 0 650 714 | 5/1995 |
| EP | 0715-840 | 6/1997 |
| JP | 3-162854 | 12/1991 |
| WO | WO 97/43994 | 11/1997 |
| WO | WO 99/14039 | 3/1999 |
| WO | WO 99/16400 | 4/1999 |

OTHER PUBLICATIONS

Definition of "fiber" and "nonwoven" Materials Handbook 4, pp. 1991.

*Primary Examiner* — Jacqueline F Stephens
(74) *Attorney, Agent, or Firm* — Brinks Hofer Gilson & Lione (57) ABSTRACT

A disposable diaper has a covering member adapted to cover a wearer's crotch and waist regions. The covering member includes an elastically stretchable first layer and an inelastically stretchable second layer formed with a plurality of continuous fibers. The continuous fibers are fixed to the first layer in at least two bonding zones. The covering member presents a particularly large value of L/D, a ratio of a length L of each continuous fiber and a distance D in straight line between each pair of the adjacent bonding zones.

9 Claims, 8 Drawing Sheets

DISPOSABLE DIAPER AND PROCESS FOR MAKING THE SAME

RELATED APPLICATIONS

The present application is a continuation of U.S. patent application Ser. No. 09/864,836, filed May 24, 2001 to which priority is claimed under 35 U.S.C. §120 and through which priority is claimed under 35 U.S.C. §119 to Japanese Priority Patent Application No. 2000-160909, filed May 30, 2000.

BACKGROUND OF THE INVENTION

This invention relates to a disposable diaper and a process for making the same.

Japanese Patent Application Publication No. 1991-162854A describes pants-type or brief-type undergarments that comprise an elastically stretchable topsheet, an elastically stretchable backsheet, elastic members extending along transversely opposite side edge portions of a crotch region so as to be associated with leg-openings and elastic members extending longitudinally opposite end portions of front and rear waist regions so as to be associated with a waist-opening. A water-absorbent core member may be disposed between the topsheet and the backsheet to use this undergarment as a disposable diaper. With such diaper, according to the description in the Publication, elastic stretchability of the topsheet and the backsheet serves to offer a good fitness and the sealing effect of the elastic members associated with the leg-openings serves to prevent sideways leaking of excretion from occurring along the leg-openings as the diaper is put on the wearer's body.

The disposable diaper of prior art enables the topsheet and the backsheet to be stretched so as to offer good fitness around the wearer's waist as the diaper is put on the wearer's body. However, stretching of the topsheet and the backsheet affects the elastic members associated with the leg-openings and tends to partially disengage the elastic members from the wearer's legs, thereby deteriorating the sealing effect of the elastic members. As a consequence, there is an anxiety that sideways leaking of excretion might occur along the elastic members associated with the leg-openings.

SUMMARY OF THE INVENTION

It is an object of this invention to provide a disposable diaper designed so that a wearer's crotch and waist regions can be covered by an elastically stretchable covering member without deteriorating a desired effect of preventing excretion leakage from occurring around wearer's legs.

According to an aspect of this invention, there is provided a disposable diaper comprising an elastically stretchable covering member adapted to cover a wearer's crotch and waist regions and a liquid-absorbent core member sandwiched between a liquid-pervious sheet destined to come in contact with skin of the diaper wearer and the covering member.

According to this invention the covering member consists of an elastically stretchable first layer and an inelastically stretchable second layer formed with a plurality of continuous fibers, the continuous fibers being fixed to the first layer in at least a pair of bonding zones that are spaced apart from each other so that a ratio of $L_1/D_1$, where $L_1$ is a length of said continuous fibers extending between a first pair of said bonding zones in a first zone on said covering member and $D_1$ is a distance in a straight line between said first pair of bonding zones in said first zone of said covering member is larger than a ratio of $L_2/D_2$, where $L_2$ is a length of said continuous fibers extending between a second pair of said bonding zones in a second zone on said covering member and $D_2$ is a distance in a straight line between said second pair of bonding zones in said second zone of said covering member.

Another aspect of this invention concerns a process for making a disposable diaper comprising an elastically stretchable covering member adapted to cover a diaper wearer's crotch and waist regions and a liquid-absorbent core member sandwiched between a liquid-pervious sheet destined to come in contact with skin of the diaper wearer and the covering member.

According to this invention the process comprises steps of bonding an elastically stretchable first layer destined to form the covering member and a second layer formed with a plurality of inelastically stretchable continuous fibers together using a plurality of intermittently formed bonding zones to form a composite sheet and stretching only a portion of the composite sheet in one direction so that the first layer of the stretched portion may be elastically stretched together with the continuous fibers. After stretching, the composite sheet is allowed to contract under a contractile force of the first layer to form the covering member.

DETAILED DESCRIPTION OF THE PREFERRED EMBODIMENTS

Details of the disposable diaper and the process for making the same according to the present invention will be more fully understood from the description given hereunder with reference to the accompanying drawings.

Figure 1:
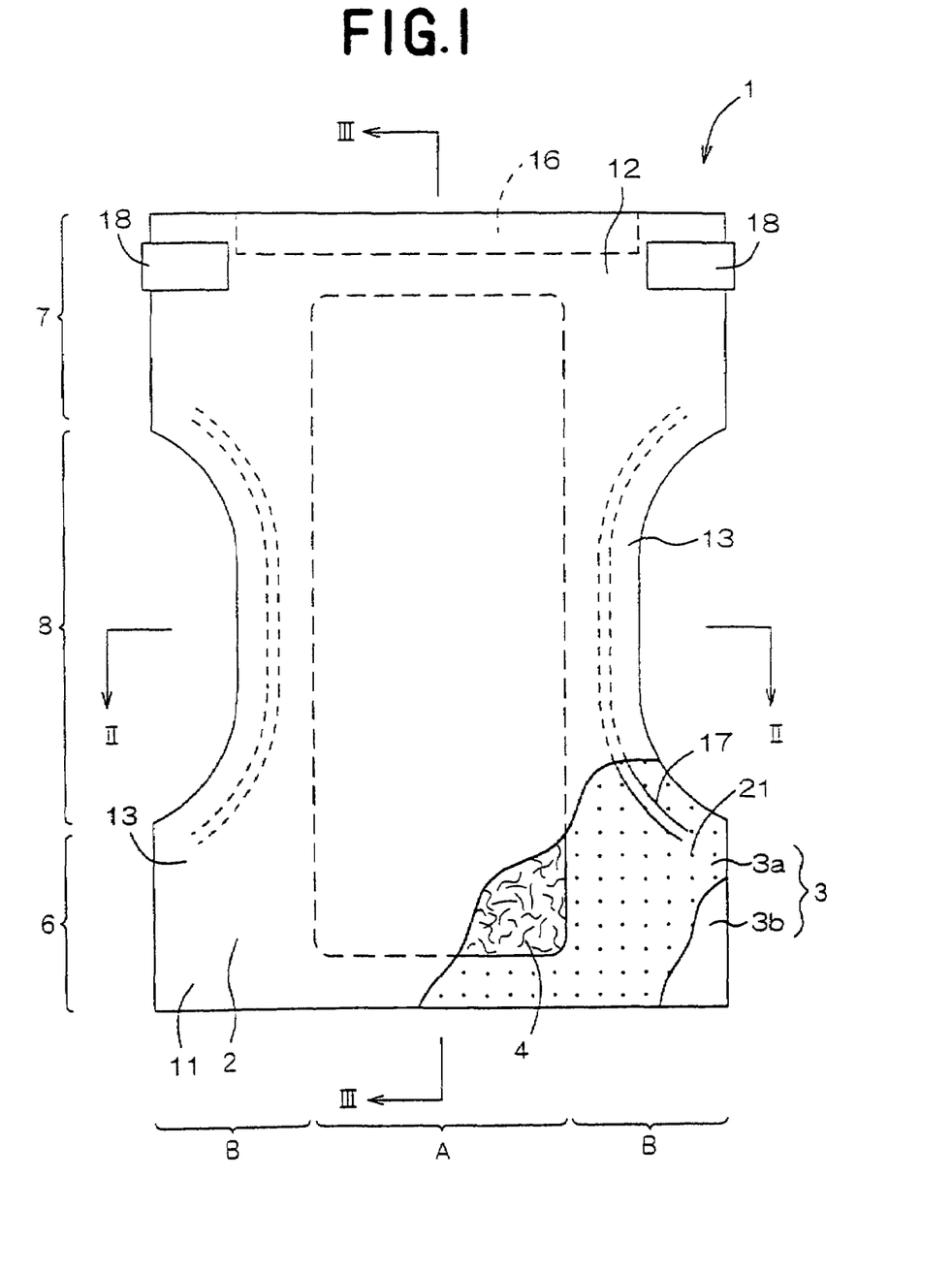
FIG. 1 is a plan view of disposable diaper as partially broken away.

A disposable diaper 1 shown by FIG. 1 in a plan view as partially broken away comprises a liquid-pervious topsheet 2, a liquid-impervious backsheet 3 and a body fluid absorbent core member 4 disposed between the topsheet 2 and the backsheet 3. The backsheet 3 is formed with an inside sheet 3a and an outside sheet 3b. The diaper 1 is composed, in its longitudinal direction, of a front waist region 6, a rear waist region 7 and a crotch region 8 extending between these two waist regions 6, 7. The topsheet 2 and the backsheet 3 are placed upon one another and bonded to each other over portions of the topsheet 2 and backsheet 3 that extend outward beyond a peripheral edge of the core member 4 so as to form a front flap 11, a rear flap 12 and a pair of side flaps 13 that are adapted to cover a crotch and a waist of a diaper wearer. The rear flap 12 has an elastic member 16 extending transversely of the diaper 1 that is bonded under tension to inner surface of at least one of the topsheet 2 and the backsheet 3 in order to be associated with a waist-opening. The side flaps 13 have elastic members 17 that extend longitudinally of the diaper 1 and are bonded under tension to the inner surface of at least one of the topsheet 2 and the backsheet 3 in order to be associated with respective leg-openings. In the rear waist region 7, a pair of tape fasteners 18 are attached to side edge portions of the side flaps 13, respectively.

The topsheet 2 is elastically stretchable and may be formed, for example, from a nonwoven fabric made of elastically stretchable filaments. The topsheet 2 is elastically stretchable at least transversely of the diaper 1 and, more preferably, along its length as well as along its width.

The inside sheet 3a of the backsheet 3 is liquid-impervious and formed from a sheet that is elastically stretchable transversely of the diaper 1 and, more preferably, is elastically stretchable along its length as well as along its width. The outside sheet 3b comprises a plurality of inelastically stretchable continuous fibers 20 (See FIG. 4) accumulated on one surface of the inside sheet 3a so as to form a sheet and are bonded to the one surface in a plurality of bonding zones 21 (See FIGS. 4A and 4B).

Figure 2:
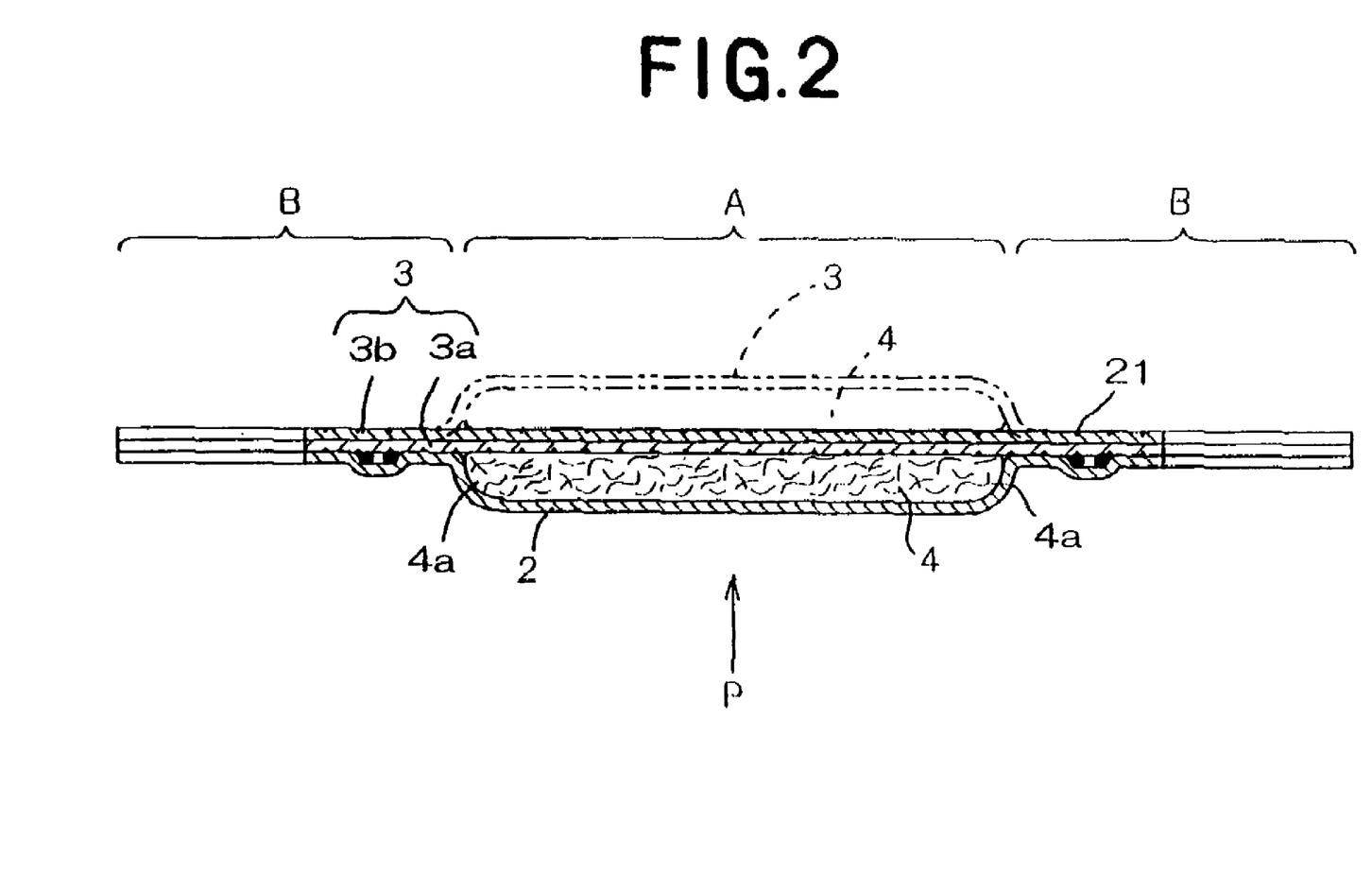
FIG. 2 is a sectional view taken along a line II-II in FIG. 1.
Figure 3:
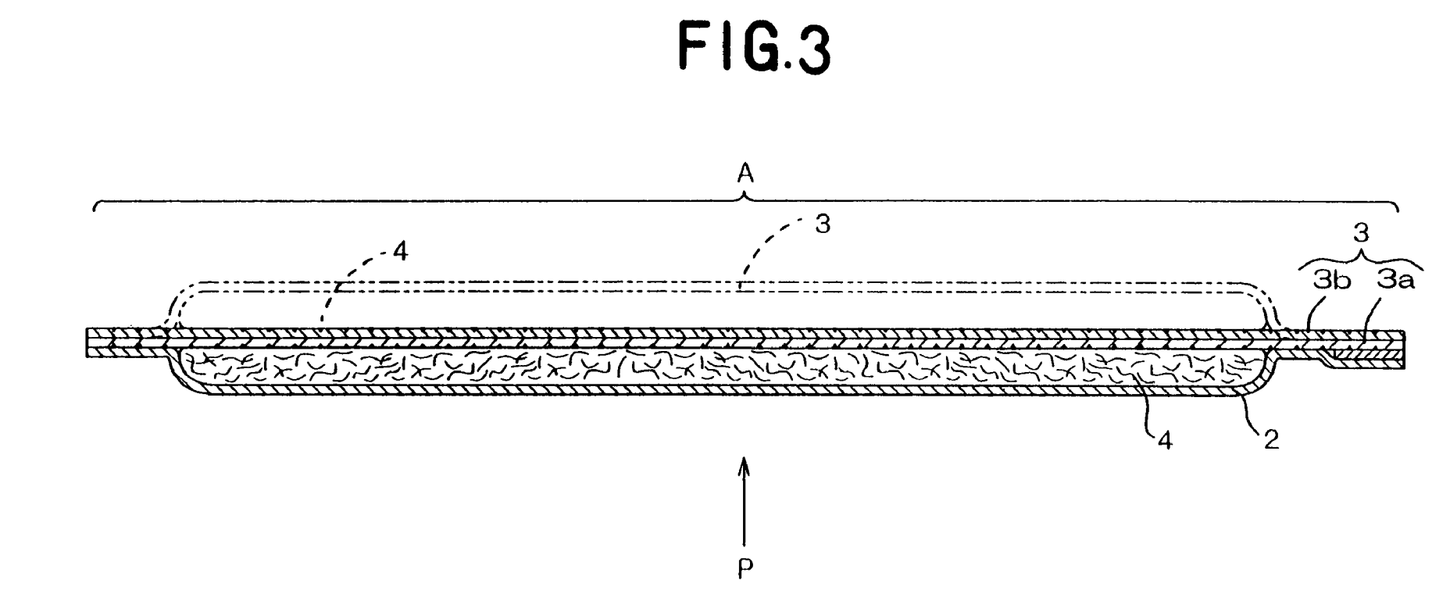
FIG. 3 is a sectional view taken along a line III-III in FIG. 1.

FIGS. 2 and 3 are sectional views taken along lines II-II and III-III in FIG. 1, respectively. In the diaper 1, the backsheet 3 is substantially flat and the core member 4 protrudes from the backsheet 3 toward the topsheet 2 (downward as viewed in FIGS. 2 and 3). The backsheet 3 is divided at least transversely into a range A extending in the middle zone and ranges B extending on both sides of the range A with the range A being more easily stretched than the ranges B. According to one preferred embodiment, the transversely middle zone having range A presents a stress of 0.25~2 N as measured on a test piece having a width of 25 mm as this zone A is stretched by 20%. This value is less than 80%, more preferably less than 50% of a stress presented by each of the ranges B as they are stretched by 20%. The topsheet 2 is stretchable transversely of the diaper 1 as easily as or more easily than the range A of the backsheet 3. The range A extends to the vicinity of transversely opposite side edges 4a, 4a of the core member 4 transversely of the diaper 1 and extends substantially over a full length of the backsheet 3 longitudinally of the diaper 1.

Only the range A of the backsheet 3 is deformed as indicated by chain lines in FIG. 2. The core member 4 shifts its position so as to protrude outwardly of the diaper 1 when the diaper 1 is put on a wearer's body with the topsheet 2 placed against the wearer's skin under pressure P exerted on the core member 4 (See FIGS. 2 and 3). The pressure P is adequately dampened by the stretching of the range A to avoid exerting pressure on the elastic members 17 of the leg-openings via the ranges B. Thus, there is no apprehension that the desired fitness of the elastic members 17 around the wearer's legs might be adversely affected by the pressure P. In this way, the elastic members 17 associated with the leg-openings cooperate with the ranges B, which are less stretchable than the range A, so to maintain the desired fitness of the diaper 1 around the wearer's legs. It is unnecessary for such diaper 1 to use elastic members 17 associated with the leg-openings that have a relatively high stretch stress to compensate for the influence of the pressure P. With such diaper 1 according to the present invention, there is no anxiety that the elastic members 17 will have a relatively high stretch stress that might be unacceptably pressed around the wearer's legs.

Figure 4A:
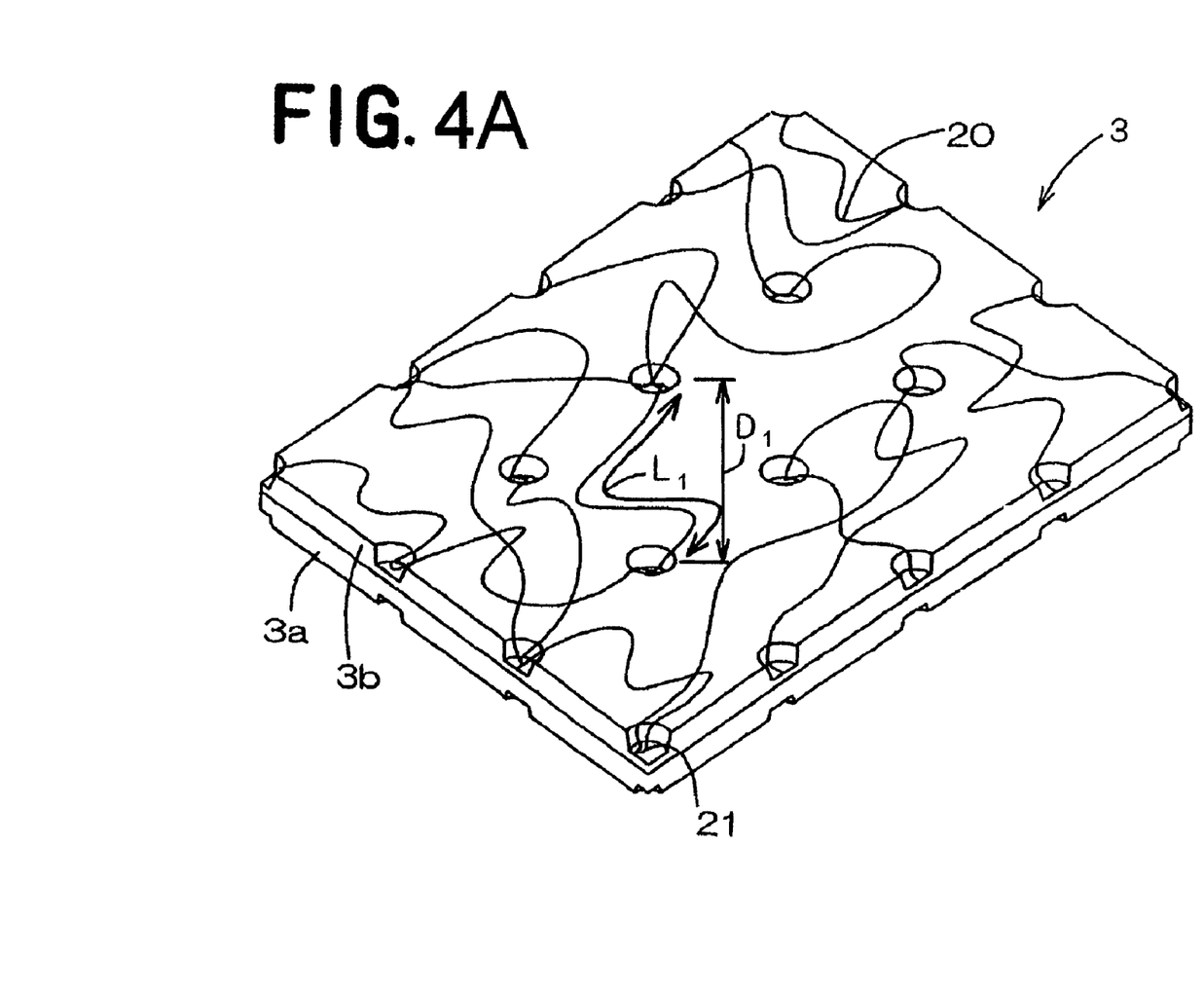
FIG. 4A is a fragmentary perspective view of the backsheet taken from range A in FIG. 2.
Figure 4B:
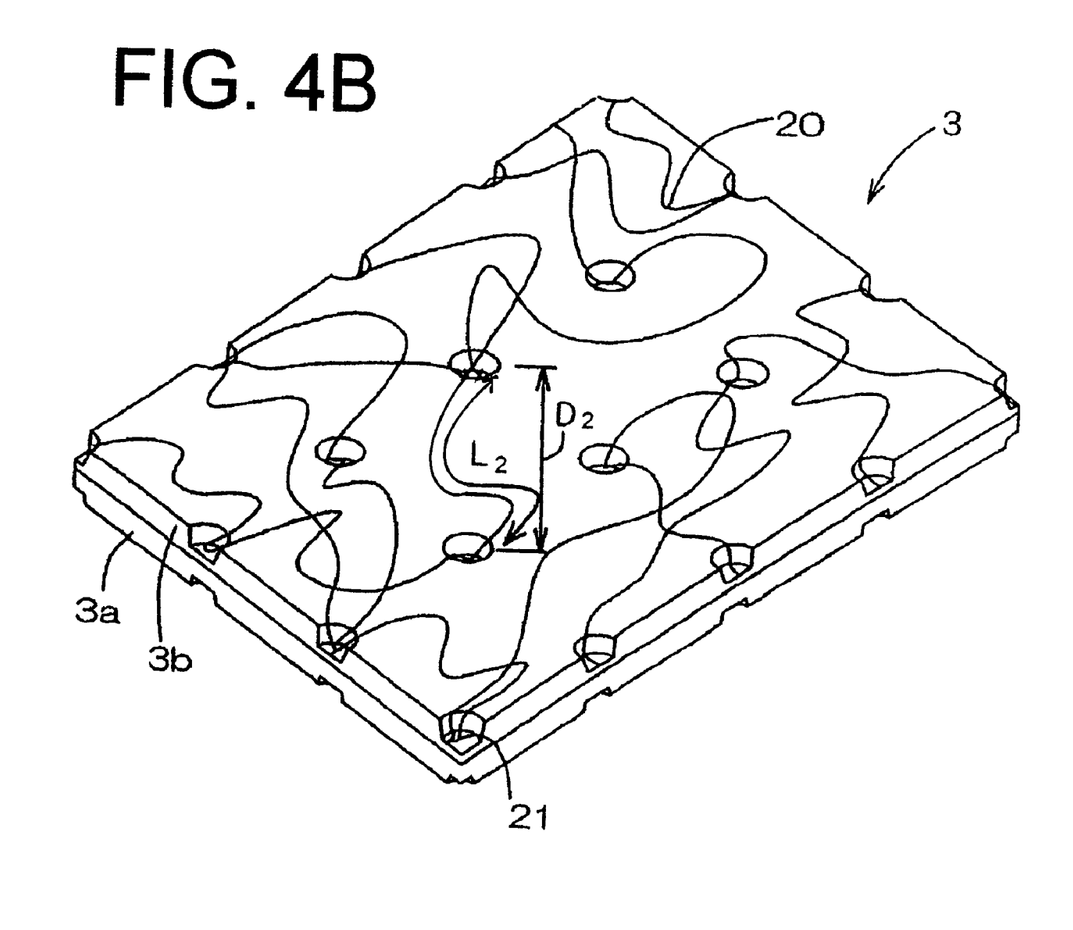
FIG. 4B is a fragmentary perspective view of the backsheet taken from range B in FIG. 2.

FIG. 4A is a fragmentary perspective view of the backsheet 3 taken from range A in FIG. 2 and FIG. 4B is a fragmentary perspective view of the backsheet taken from range b in FIG. 2. The inside sheet 3a has a basis weight of 10~100 g/m² and is formed from an elastic material such as styrene-based elastomer or urethane-based elastomer. The outside sheet 3b has a basis weight of 8~50 g/m² and is formed from a sheet-like accumulation of inelastically stretchable continuous fibers 20 such as polypropylene, ethylene/propylene copolymer or ethylene/propylene/butene copolymer fibers. The inside and outside sheets 3a, 3b are bonded together in bonding zones 21 that are formed intermittently transversely of the diaper 1, and more preferably, transversely and longitudinally of the diaper 1. In these bonding zones 21, the inside and outside sheets 3a, 3b are bonded together by fusion or adhesion.

Each of the continuous fibers 20 has a length L and describes a curve between each pair of the adjacent bonding zones 21, 21 in which the continuous fibers 20 are fixed to the inside sheet 3a. D designates a distance along a straight line connecting each pair of the adjacent bonding zones 21, 21. The ratio L/D is equal to 1 or larger. The ratio $L_1/D_1$ in the range A of the backsheet 3 is larger than the ratio $L_2/D_2$ in the ranges B (Note: FIGS. 4A and 4B are illustrative only and not drawn to depict relative proportions and the subscripts "1" and "2" are used herein to distinguish L and D for each of the ranges A and B). In other words, the range A is more easily stretchable than the ranges B transversely as well as longitudinally, at least transversely of the diaper 1. During an early stage of transversely stretching the backsheet 3, the inside sheet 3a is elastically stretched in the range A and the continuous fibers 20 are reoriented so as to be straightened between the respective pairs of the adjacent bonding zones 21, 21 in which these continuous fibers 20 are fixed to the inside sheet 3a. So far as the continuous fibers 20 are merely reoriented and substantially not stretched, the force required to stretch only the inside sheet 3a is sufficient to stretch the range A. After the early stretching stage has been completed and the continuous fibers 20 have been straightened, a considerable force is required to stretch the inside sheet 3a together with the outside sheet 3b comprising the continuous fibers 20 in the range A. On the other hand, in the ranges B of the backsheet 3 the ratio of $L_2/D_2$, i.e., a ratio the length $L_2$ of the continuous fibers 20 to the distance $D_2$ in a straight line between the respective pairs of the adjacent bonding zones 21, 21 is substantially smaller than the ratio of $L_1/D_1$ in the range A and therefore, a considerable force is required to stretch the inside sheet 3a together with the outside sheet 3b transversely of the diaper 1 after the early stage of stretching the backsheet 3.

As has been described above, the topsheet 2 is elastically stretchable while the backsheet 3 has the range A that requires no large force to stretch this range and the ranges B that require a considerable force to stretch these ranges. Accordingly, the pressure P exerted on the core member 4 by the wearer's body via the topsheet 2 as the diaper 1 is put on the wearer's body is well absorbed by stretching of the range A, as indicated by the imaginary lines in FIGS. 2 and 3. In this manner, there is substantially no possibility that the pressure P might be exerted on the ranges B also and affect the elastic members 17 associated with the leg-openings.

Figure 5:
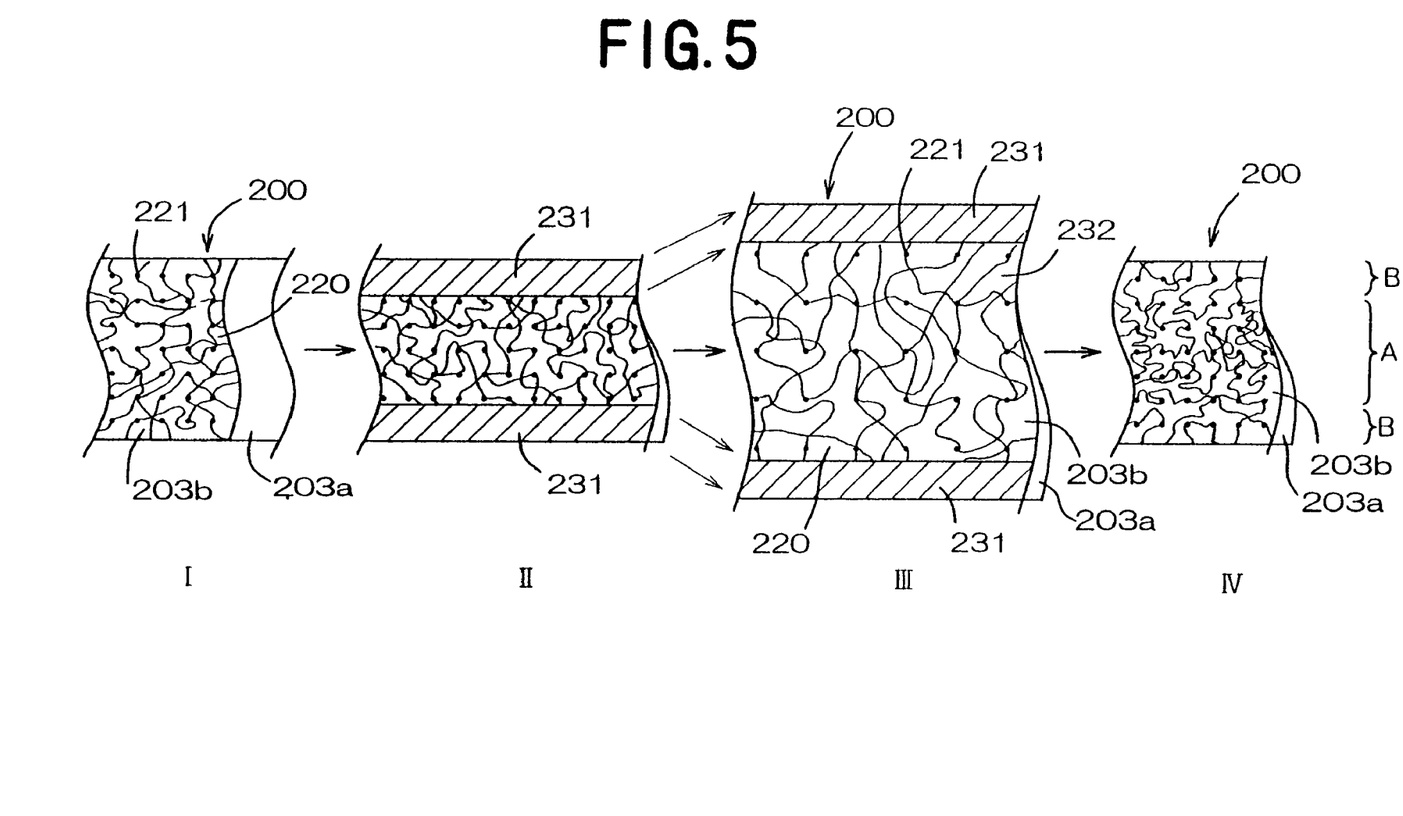
FIG. 5 is a diagram illustrating a process for making the backsheet.

FIG. 5 is a diagram illustrating a part of the process for making the backsheet 3. In step I, continuous fibers 220 destined to form the outside sheet 3b are discharged from a plurality of extruding nozzles (not illustrated) and accumulated onto one surface of elastically stretchable web 203a destined to form the inside sheet 3a of the backsheet 3. Then, a plurality of bonding zones 221 are intermittently formed in which stretchable web 203a and continuous fibers 220 are welded together to form composite web 200 which is, in turn, fed from the left as viewed in FIG. 5.

In step II, transversely opposite side edge regions 231 indicated by oblique lines of the composite web 200 are clamped so that these side edge portions 231 would not be stretched in the subsequent steps.

In step III, a transversely middle region 232 of the composite web 200 which is free from the clamping effect is transversely stretched by at least 50% or more, preferably by 80% or more, and more preferably by 200% or more. In this step III, the stretchable web 203a is elastically stretched and the continuous fibers 220 are inelastically stretched between the respective pairs of the adjacent bonding zones 221, 221, in other words, stretched under plastic deformation. Along the transversely opposite side edge regions 231, both the stretchable web 203a and the continuous fibers 220 are not stretched.

In step IV, the composite web 200 having been stretched is contracted under a contractile force of the stretchable web 203a and thereafter the composite web 200 is unclamped.

The contracted composite web 200 obtained in the manner as has been described may be cut into an appropriate length to obtain the backsheet 3 of FIG. 1 wherein the middle region 232 and the side edge regions 231 of the composite web 200 define the inside sheet 3a and the outside sheet 3b of the backsheet 3, respectively. The continuous fibers 220 and the bonding zones 221 correspond to the continuous fibers 20 and the bonding zones 21, respectively. In the backsheet 3 obtained through these steps, the continuous fibers 20 extending within the range A have been stretched at a higher ratio than the continuous fibers 20 extending in the zones B and consequently the formers are thinner than the latter. The ratio $L_1/D_1$ between each pair of the adjacent bonding zones 21, 21 is larger in the range A than the ratio $L_2/D_2$ in the ranges B. The outside sheet 3b comprising the continuous fibers 20 is more bulky in the range A than in the ranges B since the continuous fibers 20 have been stretched at a higher ratio in the range A than in the ranges B. The backsheet 3 offers more flexible and soft touch in the range A than in the ranges B.

Figure 6:
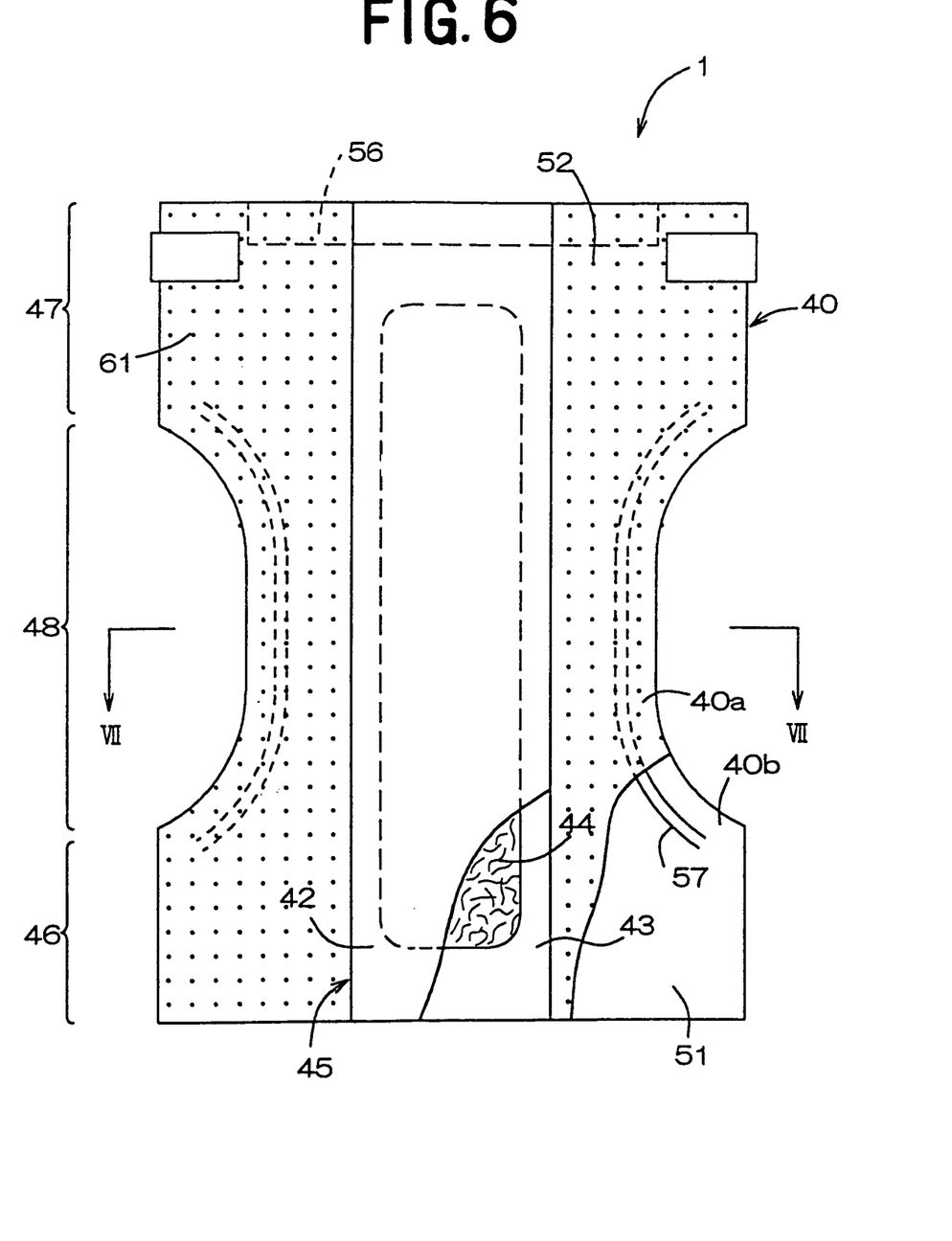
FIG. 6 is a view similar to FIG. 1 showing one preferred embodiment of this invention.
Figure 7:
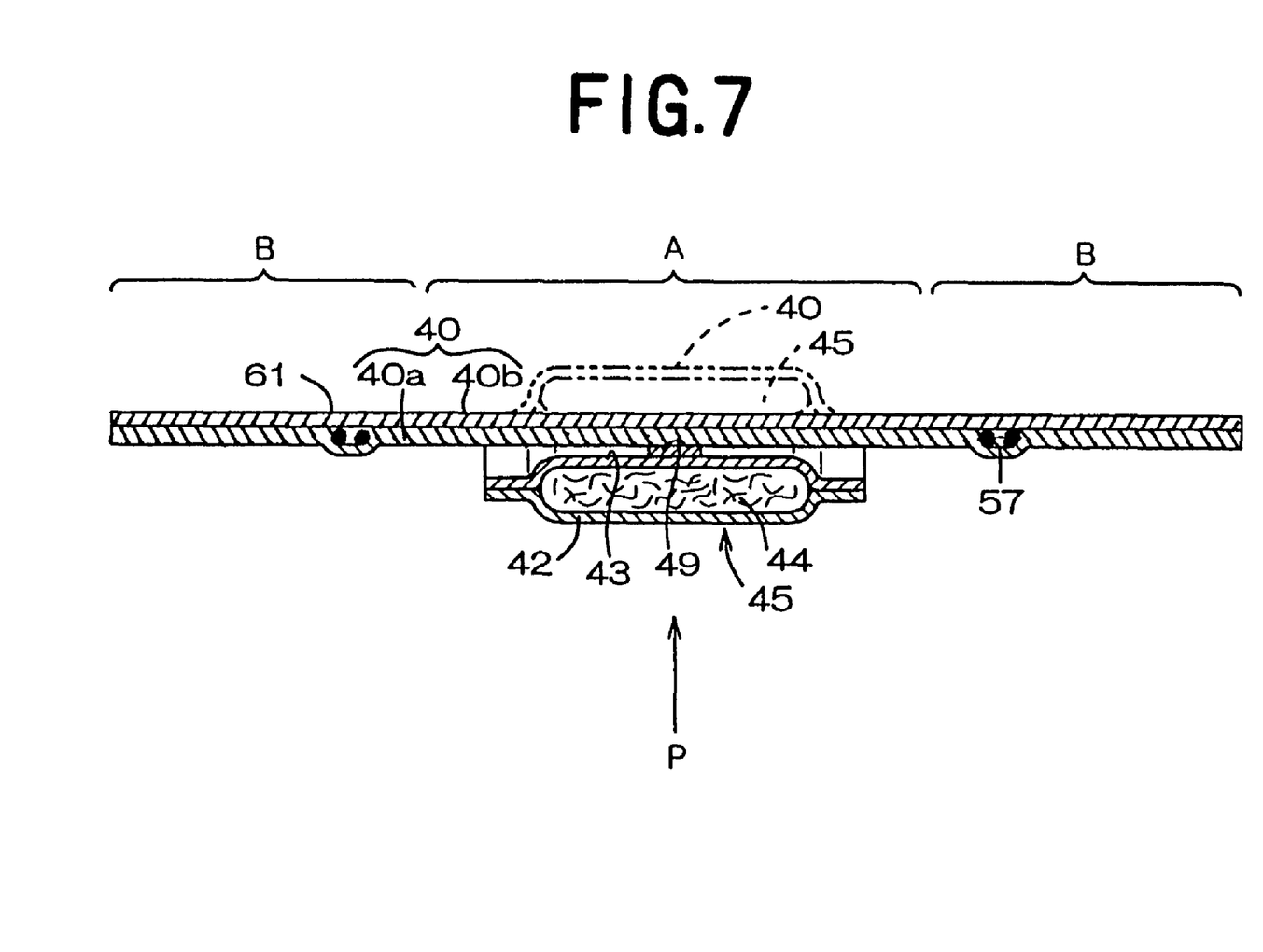
FIG. 7 is a sectional view taken along a line VII-VII in FIG. 6.

FIG. 6 is a view similar to FIG. 1 showing one preferred embodiment of this invention and FIG. 7 is a sectional view taken along a line VII-VII in FIG. 6. The diaper 1 illustrated in FIGS. 6 and 7 has a covering member 40 adapted to cover crotch and waist regions of the wearer and an absorbent member 45 adapted to absorb body fluids. The absorbent member 45 comprises a core member 44 lying inside the covering member 40, a liquid-pervious sheet 42 covering the core member 44 and destined to come in contact with the wearer's skin and a liquid-impervious sheet 43 lying on the side opposed to the liquid-pervious sheet 42 with the core member 44 therebetween. Both the liquid-pervious sheet 42 and the liquid-impervious sheet 43 are elastically stretchable preferably in the transverse direction, and more preferably elastically stretchable in both the transverse direction and in the longitudinal direction of the diaper 1. Portions of these sheets 42, 43 extending outward beyond a peripheral edge of the core member 44 are placed upon each other and are bonded to each other by means of hot melt adhesive 49. The covering member 40 is longitudinally composed of a front waist region 46, a rear waist region 47 and a crotch region 48 extending between the front waist region 46 and the rear waist region 47. The liquid-impervious sheet 43 longitudinally extending outward beyond the peripheral edge of the core member 44 is bonded to the inner surface of the covering member 40 along respective end portions 51, 52 thereof in the front waist region 46 and the rear waist region 47, also by means of hot melt adhesive 49. While the portion of the liquid-impervious sheet 43 extending between the end portions 51, 52 has been described to be bonded to the covering member 40 by means of hot melt adhesive, it is also possible to leave this portion unbonded to the covering member 40.

The covering member 40 comprises an elastically stretchable liquid-impervious inside sheet 40a and an outside sheet 40b formed with inelastically stretchable continuous fibers 20. These two sheets 40a, 40b are bonded together in a plurality of bonding zones 61 formed intermittently in at least in the transverse direction of the diaper 1. Transverse stretchability of such covering member 40 is substantially similar to that of the backsheet 3 shown in FIGS. 1~3. Specifically, the covering member 40 has the range A defined in the transversely middle zone thereof and the ranges B defined on both sides of the range A. In the range A, the continuous fibers 20 have been stretched at a relatively high ratio so that the covering member 40 can be easily stretched in this range A. In the ranges B, the continuous fibers 20 substantially have not been stretched and therefore it is not so easy to stretch the covering member 40 in these ranges B. Along the end portion 52 of the rear waist region 46, an elastic member 56 associated with the waist-opening is disposed between the inside sheet 40a and the outside sheet 40b and bonded to the inner surface of at least one of these sheets 40a, 40b.

In the case of this diaper 1 also, the pressure P exerted on the absorbent member 45 including the core member 44 is sufficiently absorbed by the range A of the covering member 40, having been stretched to prevent the pressure P from affecting elastic members 57 associated with the respective leg-openings. As a consequence, it is not apprehended that the pressure P applied to this diaper will cause the members 57 to be disengaged from the wearer's legs and thereby cause sideways leaking of excretion.

While this invention has been described hereinabove with respect to the open-type diaper 1 as a typical embodiment, this invention is also applicable to a pants-type diaper. It is not essential to define the range A of the member covering the crotch and waist regions in which this member is more easily stretchable than the remaining zones in the transversely middle zone of the member, since the range in which this member is more easily stretchable than the remaining zones may be selectively defined in any desired zone.

In the disposable diaper according to this invention, the covering member adapted to cover the crotch and the waist regions is formed so that the covering member can be more easily stretched in its transversely middle zone than in its transversely opposite side edge portions. With this unique arrangement, the pressure exerted from the wearer's body upon the absorbent core member as the diaper is put on the wearer's body is substantially prevented from affecting the elastic members associated with the leg-openings. In this way, it is possible to eliminate an anxiety that the elastic members might be disengaged from the legs and, as a result, excretion might leak sideways.

What is claimed is:

1. A disposable diaper comprising;
   an elastically stretchable covering member for covering a diaper wearer's crotch and waist regions;
   a liquid-pervious sheet having a skin contactable surface for contacting with skin of said diaper wearer;
   a liquid-absorbent core member sandwiched between said liquid-pervious sheet and said covering member;
   discrete elastic members provided along transverse side edges of said diaper to extend circumferentially along leg-openings that are defined when the diaper is put on the diaper wearer;
   said covering member consisting of an elastically stretchable first layer and an inelastically stretchable second layer formed of a plurality of continuous fibers, and said continuous fibers being fixed to said elastically stretchable first layer in bonding zones spaced apart from each other so that a ratio of $L_1/D_1$ where $L_1$ is a length of said continuous fibers extending between a first pair of said bonding zones in a centrally located first zone on said covering member and $D_1$ is a distance in a straight line between said first pair of bonding zones in said first zone of said covering member is larger than a ratio of $L_2/D_2$, where $L_2$ is a length of said continuous fibers extending between a second pair of said bonding zones in a second zone on said covering member and $D_2$ is a distance in a straight line between said second pair of bonding zones in said second zone of said covering member, whereby said covering member is more easily stretched in a direction away from the skin contactable surface in said first zone than in said second zone of said covering member, and said first zone being adjacent said liquid-absorbent core member and at least substantially coextensive with said liquid-absorbent core member, so that pressure exerted on said covering member by said liquid-absorbent core member will stretch the first zone in said direction of the skin contactable surface without exerting any pressure on said discrete elastic members
wherein said continuous fibers of said inelastically stretchable second payer are fixed to said elastically stretchable first layer in bonding zones while said elastically stretchable first layer is in an unstretched state.

2. The diaper according to claim 1, wherein said first zone is defined in a transversely middle zone of said diaper.

3. The diaper according to claim 1, wherein said elastically stretchable first layer is formed of an elastically stretchable film.

4. The diaper according to claim 1, wherein said continuous fibers of said inelastically stretchable second layer are made of polypropylene.

5. The diaper according to claim 1, wherein said elastically stretchable first layer is formed from a liquid-impervious sheet and lies inside said inelastically stretchable second layer.

6. The diaper according to claim 1, wherein said elastically stretchable first layer is formed from a liquid-impervious sheet and lies inside said inelastically stretchable second layer so that said elastically stretchable first layer functions as a liquid-impervious backsheet for said liquid-absorbent core member.

7. The diaper according to claim 1, wherein said elastically stretchable first layer is formed of a nonwoven fabric made of crimped fibers.

8. The diaper according to claim 1, wherein said continuous fibers of said inelastically stretchable second layer are made of propylene copolymers.

9. The diaper according to claim 1, wherein said first zone presents a stress of 0.25-2 N/25 mm width as said first zone is stretched by 20%, which is less than 80% if stress presented by each of said second zones is stretched by 20%, and said liquid-pervious sheet is stretchable transversely of said diaper as easily as or more easily than said first zone of said covering zone.

* * * * *